(12) United States Patent
Thorne, Jr. et al.

(10) Patent No.: US 7,785,312 B2
(45) Date of Patent: Aug. 31, 2010

(54) CONVENIENCE IV KITS AND METHODS OF USE

(75) Inventors: Gale Harison Thorne, Jr., Bountiful, UT (US); Evan William Call, Bountiful, UT (US); Gale Harrison Thorne, Bountiful, UT (US)

(73) Assignee: IntraVena, LLC, Bountiful, UT (US)

( * ) Notice: Subject to any disclaimer, the term of this patent is extended or adjusted under 35 U.S.C. 154(b) by 221 days.

(21) Appl. No.: 12/012,837

(22) Filed: Feb. 6, 2008

(65) Prior Publication Data
US 2009/0194453 A1    Aug. 6, 2009

(51) Int. Cl.
*A61M 31/00* (2006.01)
(52) U.S. Cl. ................................................. 604/500
(58) Field of Classification Search ................. 604/500, 604/506, 181, 183, 82; 206/571, 570
See application file for complete search history.

(56) References Cited

U.S. PATENT DOCUMENTS

| | | | |
|---|---|---|---|
| 5,290,259 A | 3/1994 | Fisher | |
| 5,389,070 A | 2/1995 | Morell | |
| 5,810,773 A | 9/1998 | Pesnicak | |
| 5,947,890 A | 9/1999 | Spencer et al. | |
| 6,158,467 A | 12/2000 | Loo | |
| 6,287,265 B1 | 9/2001 | Gleason | |
| 6,610,033 B1 | 8/2003 | Melanson et al. | |
| 6,936,033 B2 | 8/2005 | McIntosh | |
| 2004/0035743 A1* | 2/2004 | Tighe et al. | 206/571 |
| 2006/0275336 A1* | 12/2006 | Du Plessis | 424/423 |

OTHER PUBLICATIONS

Product Specification, Codan, May 15, 2009, CYTO-IBC.

* cited by examiner

*Primary Examiner*—Melba Bumgarner
(74) *Attorney, Agent, or Firm*—Gale H. Thorne

(57) ABSTRACT

A convenience kit assembled and organized to measure, fill and dispense medication and flush solutions to patients through connections to patient lines and catheters while improving safety and efficacy of such procedures by requiring fewer post-sterilization makes and breaks when compared to similar filling and dispensing methods using conventional components. Further the kit improves flush compliance by facilitating dispensing of flush solutions and decreases likelihood of infections by providing for flushing of patient lines and catheter connecting fittings without any additional line breaks. The kit is provided in resealable, tamper evident kit packaging which permits sealed transport of kit parts after initial opening and follow-on parts use. Convenience of operation is provided by a two syringe assembly which is operable by a single hand by which selective dispensing is accomplished from either of the two syringes while obstructing flow from the other syringe. The kit comprises a clip for the stabilizing the two syringe assembly for use by a single hand.

5 Claims, 12 Drawing Sheets

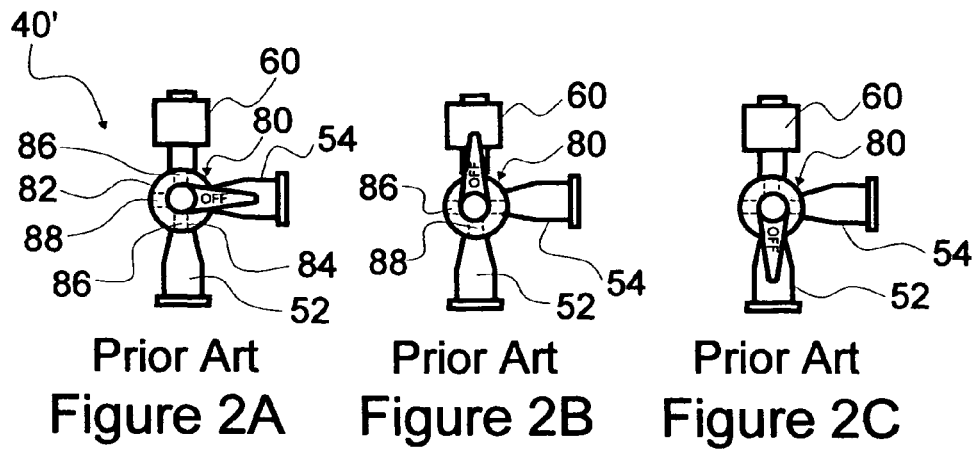
Prior Art
Figure 2A
Prior Art
Figure 2B
Prior Art
Figure 2C
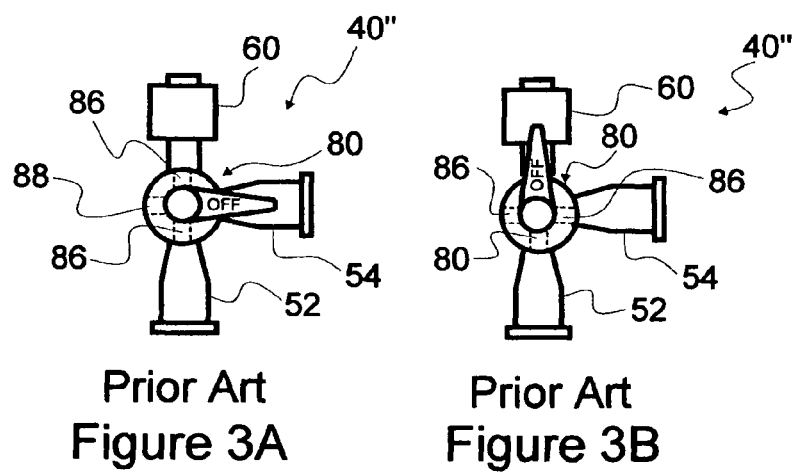
Prior Art
Figure 3A
Prior Art
Figure 3B
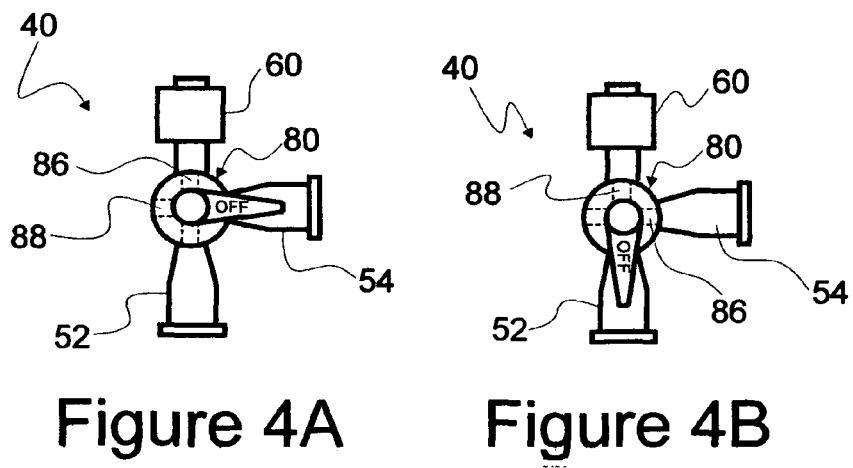
Figure 4A
Figure 4B

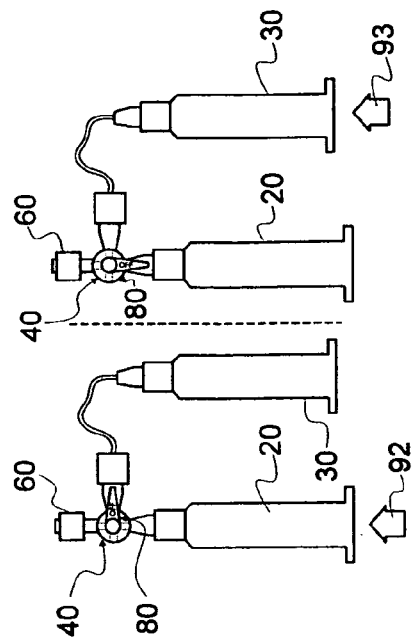
Figure 6A
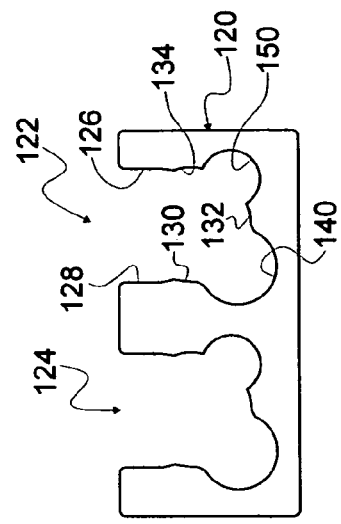
Figure 6B
Figure 8
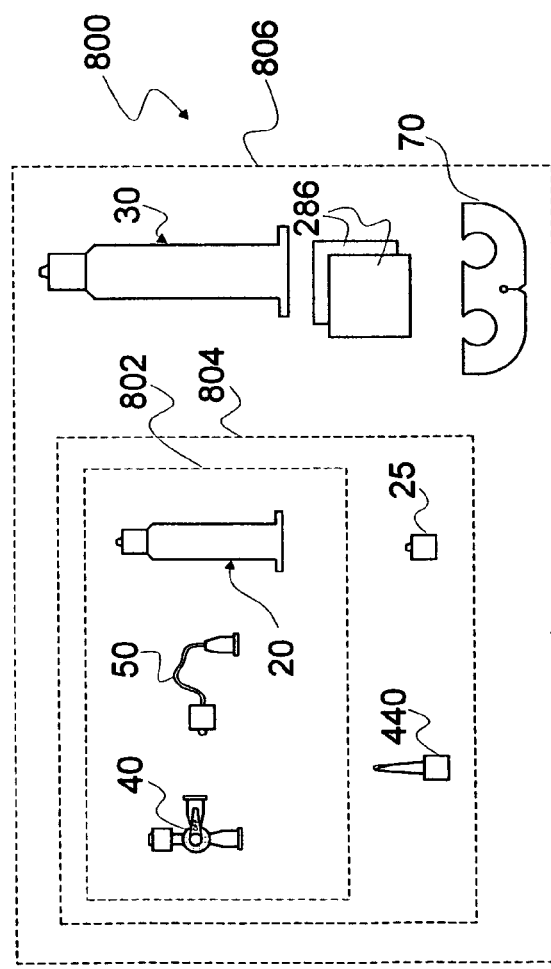
FIGURE 25

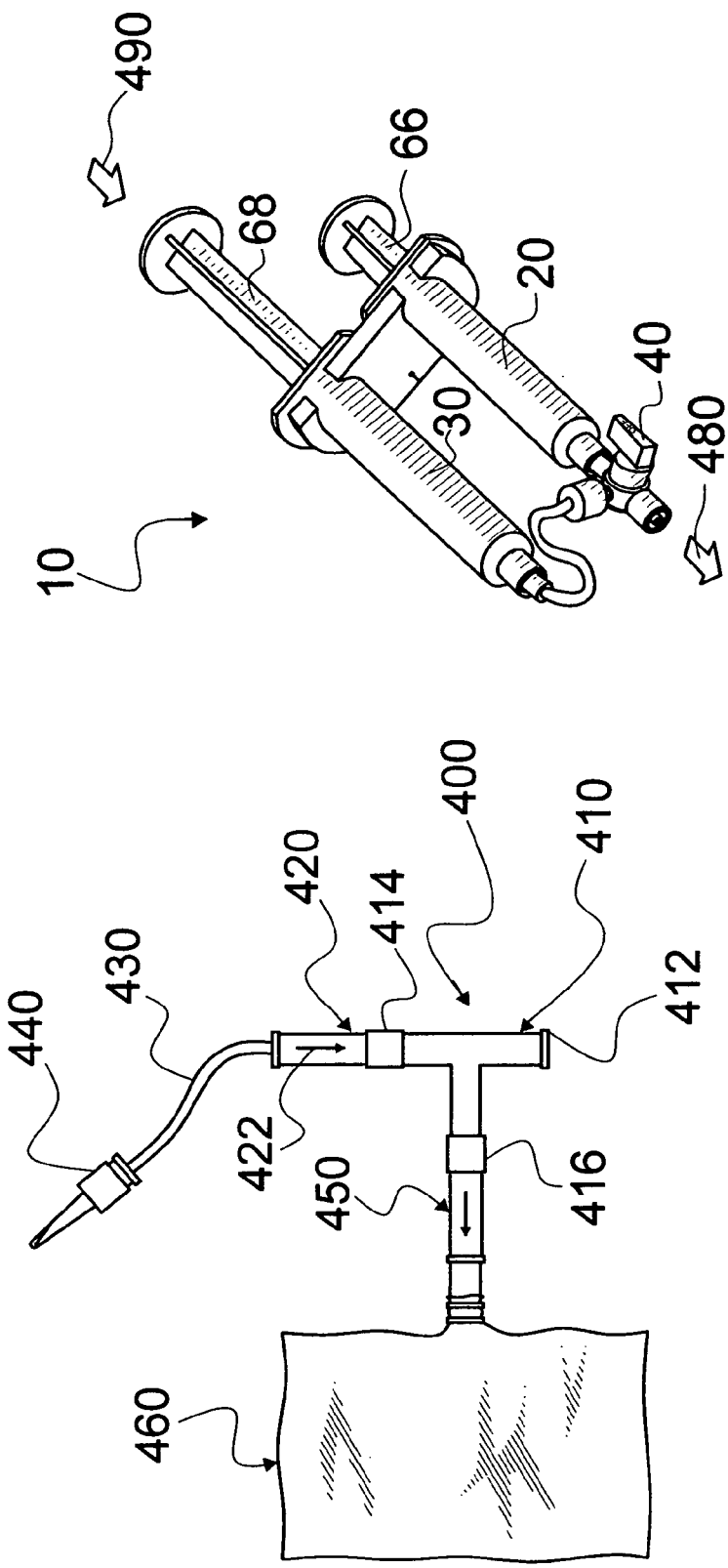

CONVENIENCE IV KITS AND METHODS OF USE

FIELD OF INVENTION

This invention relates generally to medical intravenous administration syringes, specifically including pre-filled flush syringes. It is also particularly related to kits and to methods which employ preassembled parts which are substantially fabricated for the purpose of achieving a significant decrease in need for making and breaking line connections and other product manipulations.

BACKGROUND AND DESCRIPTION OF RELATED ART

During the past decade, a great effort has been made by the medical community to decrease concerning and sometimes tragic effects of accidental needle sticks. A revolution in medical needle products and their use has resulted in significant growth of a relatively new safety needle industry. In addition, use of IV catheters has significantly reduced the number of needle sticks required in contemporary medical practice.

However, increased use of catheters (nearly every hospital patient is currently fitted with an IV catheter shortly after admission) has resulted in a generation of problems and procedures related to catheter safety. Recognition of some catheter use problems has resulted in the following principles, considerations and guidelines:

A basic principle taught in IV therapy is that every IV delivered medication should be flushed. This principle is intended to help prevent incompatible drug mixing and assure delivery of a timely, complete dose. Unfortunately, many nurses forget to flush or assume that a running IV will flush a Y-injection site which leaves small amounts of medication in the Y-site where a potentially incompatible drug may cause a problem. Many institutions claim that a high catheter replacement rate in central lines is a direct consequence of a failure to consistently flush lines after each medication injection into the IV line.

A Jul. 5, 2005, PHC4 Research Brief entitled "Hospital-acquired Infections in Pennsylvania" reported that clinician-caused (nosocomial) bloodstream infection rates in Pennsylvania may be as high as 21,458 per year at a treatment cost of $861 million and mortality rate of 25.6% in 2004 alone. Such treatment costs in hospitals extrapolate to a $20.3 billion cost and over 80,000 deaths per year in the United States. Additional studies that cite similar increases in infection rates led to the "100,000 lives Campaign" instigated by the Institute for Healthcare Improvements, Cambridge, Mass., which is intended to save lives that would otherwise be lost due to nosocomial infection rates. Clinicians who work in IV therapy are well schooled in knowing that "the more line breaks and line manipulations, the greater the chance for line contamination". Reducing line breaks and line manipulations, in principle, will reduce line contaminations and patient infections.

A chronic nursing shortage, projected to persist beyond 2012, places nursing time at a premium. Short-staffed healthcare facilities result in busier nurses who may be more prone to medical errors, some of which result in serious consequences for patients. A product which would save nursing time by reducing nursing steps would simplify caregiver procedures and reduce nursing steps should also most assuredly reduce clinician errors and overall healthcare costs.

A 2004 NIOSH (National Institute of Occupational Safety and Health) Safety Alert: Preventing Occupational Exposure to Antineoplastics and Other Hazardous Drugs in Healthcare Settings warns healthcare institutions about the need to provide products and procedures to protect clinicians from hazardous drug exposure. Attempts to reduce such drug exposure has resulted in use of expensive protective port attachment devices.

Thus, there exists a severe contemporary need for devices, not currently available commercially, which reduce injection site makes and breaks (see Terms and Definitions Section), reduce nurse and pharmacist time, facilitate ease of flushing and provide a greater degree of safety related to line contamination and subsequent patient infection and care-giver risk to hazardous drug exposure.

TERMS AND DEFINITIONS

Following is a list of terms and associated definitions provided to improve clarity and understanding of precepts of the instant invention:

break, n: a disconnection of a pair of medical connectors, usually as part of a medical procedure clip, n: a holder for a pair of syringes for stabilizing the syringes while performing a medical procedure crib pad, n: a pad which comprises a barrier layer and an absorbent layer and which derives its name from pediatric applications dead space, n: a volume of inaccessible fluid which is retained within a device after a procedure extension set, n: any tubing and associated connecting parts which may be used to connect a stopcock to a pre-filled syringe half-life, n: a period of time during which activity or usefulness declines by half (generally applied to drugs which deteriorate quickly when introduced into a physical system)

fitting, n: a medical connector kit, n: a group of parts, provided within a single package for a designated use luer fitting, n: a medical connector having a frustoconically shaped connecting geometry which is in common use in medical practice luer lock fitting, n: a luer fitting having a locking mechanism whereby a male and female connector are securely, but releasably affixed one to the other make, n: a connection or re-connection of a pair of medical connectors usually made as a result of a medical procedure port, n: a site for a medical connector, where through fluid is communicated to a patient line (e.g. a catheter)

pouch, n: a bag or tray resealable pouch, n: a bag or tray having a structure which permits manual resealing after interim use subkit, n: a group of parts provided as a unit within a kit being identifiably separate from other parts of the kit (on its own, a subkit could be considered to be a kit)

TPA, n: one of a set of drugs used for clearing blood-clot occluding catheters; other such drugs include stretokinase, urokinase, etc.

unitized, adj: a plurality of separate parts permanently joined to be handled and used as a single unit wrap, n: a flexible container which may be a bag or folded shield which is sealed to provide a cover in which enclosed parts are sterilized and protected until opened for use

BRIEF SUMMARY AND OBJECTS OF THE INVENTION

In brief summary, this novel invention alleviates all of the known problems related to reducing makes and breaks and decreasing contamination and increasing patient safety when dealing with catheter related injection ports and associated devices and a need to conserve nursing and pharmacist time. The invention is a dedicated convenience kit which consists of a sealed, but openable and resealable, outer pouch which contains a sealed wrap enclosing a subkit of components, which are unitized and sterilized, within the wrap and an assortment of other items, including a flush syringe, specifically needed to complete a predetermined medical procedure.

Generally, the package is used in two stages, (1) preparation and (2) delivery to a site of use. At a station where the subkit components and items are prepared for use (for example, where a syringe is filled with a prescribed drug, etc.), the package is opened for access to the wrap and other items. Preferably the station is in a controlled environment (such as in a sterile area and/or under a laminar flow hood) so that subkit components may be removed yet remain contamination free. Packaging subkit components and items separately permits the subkit components within the wrap to be sterilized (by gamma radiation, ethylene oxide, etc.) independently. Thus, other items, which need not be sterilized or which may be damaged by a selected mode of sterilization used upon the wrap, can still be delivered as part of the kit.

Importantly, those subkit components which are not separated as part of the procedure are securely affixed as a unit (unitized), one to another (such as by adhesion) to minimize makes and breaks. As an example, a syringe, for drug delivery, provided as part of the kit, is securely and permanently affixed to other subkit components through which drugs are acquired and later delivered. In this manner, the subkit components are provided to a preparer in a "ready to use" format which will not inadvertently come apart.

One of the compelling purposes of convenience kits resulting from this invention is providing an inherently associated flush syringe. As contents of a flush syringe should, in most cases, be kept disparate from a prescribed drug prior to drug delivery, it is important that a secure fluid switching component be used to controllably regulate filling and delivery pathways. For this purpose, it is preferred to use a stopcock, permanently and securely affixed to the pathway associated with the dose syringe, as the fluid controlling device. Even so, other modes of fluid regulation may be used within the scope of the invention, as an example, "Y" sites with clamps on extensions of tubing therefrom may be used. Stopcocks are commonly used in medical practice; however, a stopcock configuration for at least one convenience kit application (for hazardous drugs such as those used in oncology) is not generally available commercially. Disclosure of such a stopcock is provided in detail hereafter.

Once preparation is complete (e.g. the drug syringe prescription is filled) and the flush syringe is affixed to the subkit components, with exit pathways capped and protected, the assembled kit components are returned to the pouch. The pouch is resealed and dispatched for use. At the site of use, contents of the pouch are removed and, with but a single make, connected to a catheter dispensing port whereat the drug syringe is emptied as prescribed, followed by flush delivery to assure compliance with guidelines for flushing.

Handling two syringes affixed to a stopcock may require a fixture to stabilize one of the syringes while using the other. For such purposes, a dual syringe clip is an element of the instant invention provided to facilitate syringe handling.

Kits based upon the present invention have a variety of subkit components disposed and sterilized in each sealed wrap and also a varied assortment of other items resident in each type of kit pouch. While components and items are fixed for each particular application, a wide diversity of parts may be used for both components and items within the scope of the invention. However, in all cases, subkit components are generally affixed one to another and sterilized within a wrap to provide a "ready to use" configuration.

One example of a convenience kit, based upon the present invention, is a hazardous drug kit. While all drugs may be considered to be somewhat hazardous, such drugs as anti-neoplastic drugs used in oncology are particularly dangerous. For example, some anti-neoplastic drugs are considered extremely dangerous, even if contact is made simply upon skin as a liquid or inhaled as a vaporized product.

To alleviate the likelihood of exposing a hazardous drug to environment outside a drug filled syringe, the presence of a pre-filled flush syringe as part of a kit structure provides a unique opportunity for safety. In this case, the pre-filled syringe and drug dispensing syringe are connected to a common dispensing pathway through a stopcock. The stopcock is designed and constructed to permit only one communicating pathway from one of the syringes at a time. Thus, after the syringe is filled with drug in stage 1, the pathway from the drug syringe to the dispensing pathway is closed to the dose syringe and afterward opened to the flush syringe. Then, a predetermined, but small, amount of flush liquid is dispensed through the dispensing pathway to flush drug from the dispensing pathway and leave flush liquid at an associated connection port. Similarly in stage 2, after a desired drug volume has been dispensed from the drug syringe, a desired amount of flush liquid is dispensed through the dispensing pathway and through an attached catheter to clear both the associated catheter and connection port prior to disconnecting the kit parts from the catheter port.

Another advantage of a kit made according to the instant invention is found when administering a short half-life drug (e.g. adenosine). Short half-life drugs, administered through a catheter, must be delivered to their target organ in as short a time as possible. In such cases, it is common practice to connect two syringes to "Y" injection sites on an IV set connected to a patient catheter to permit delivery of the short half-life drug from one syringe handled by a first care-giver, followed by delivery of flush from a second syringe by a second care-giver. Having both the drug syringe and flush syringe available to a single dispensing pathway, through a stopcock, provides opportunity for a single care-giver to dispense the short half-life drug, switch the stopcock pathway and immediately dispense the flush syringe. Using the syringe stabilizing clip permits simple motion of a thumb from one syringe plunger stem to the other, while switching the stopcock, to change syringe dispensing modes.

As disclosed hereafter, various convenience kit configurations may be used for dispensing drugs and flush, and for using syringe pumps, as the dual syringe clip permits selectively displacing a syringe from the clip such that the freed syringe can be displaced into a standard syringe pump. Also, other stopcock configurations may be used to facilitate dilution of a drug in the drug syringe by solution from the flush syringe as is disclosed in detail hereafter. Other application examples for the instant invention includes emergency syringe kits, oncology drug dispensing, short half-life drug delivery and kits for home care.

Further, to show by example, advantages of using a kit made according to the present invention, for an oncology kit following are two tables (1 & 2). Table 1 summarizes a comparison of steps required by an exemplary conventional method to an associated method consistent with the instant invention. In the busy and often stressful environment of patient care, extra steps represent a penalty to patient care. Each extra step can be estimated to require a given amount of time. If, for example, each step were required to take an average of 10 seconds, time saved by the method performed according to the instant invention would amount to 110 seconds or the better part of two minutes.

TABLE 1

| General Steps | Conventional | Present Invention |
|---|---|---|
| Acquire the following parts: | | |
| Convenience kit | | 1 |
| Pre-flush syringe | 1 | |
| Post-flush syringe | 1 | |
| Gauze pads | 1 | |
| Protective pad | 1 | |
| Alcohol preps (2) | 1 | |
| Place protective and gauze pads under site | 1 | 1 |
| Swab injection site | 1 | 1 |
| Open pre-flush syringe package | 1 | |
| Open convenience kit bag and remove kit | | 1 |
| Remove cap from stopcock | | 1 |
| Remove cap from pre-flush syringe | 1 | |
| Attach kit assembly to injection site | | 1 |
| Attach pre-flush syringe to injection site | 1 | |
| Deliver pre-flush | 1 | 1 |
| Switch stopcock to dose pathway | | 1 |
| Disconnect pre-flush syringe | 1 | |
| Remove dose syringe from container | 1 | |
| Remove cap from dose syringe | 1 | |
| Attach dose syringe to injection site | 1 | |
| Deliver medication | 1 | 1 |
| Switch stopcock to flush pathway | | 1 |
| Remove dose syringe | 1 | |
| Properly dispose of dose syringe | 1 | |
| Open post-flush syringe package | 1 | |
| Remove cap from post-flush syringe | 1 | |
| Attach post-flush syringe to injection site | 1 | |
| Deliver post-medication injection flush | 1 | 1 |
| Disconnect kit assembly | | 1 |
| Disconnect post-flush syringe | 1 | |
| Properly dispose of kit (bio-hazard bag) | | 1 |
| Properly dispose of post-flush syringe | 1 | |
| Properly dispose ancillary products | 1 | 1 |
| Total steps taken | 25 | 14 |

In table 2, a comparison of makes and breaks required for operational steps by a conventional method and by a method associated with the present invention is provided:

TABLE 2

| Make or Break Step | Conventional | Present Invention |
|---|---|---|
| Remove cap from stopcock | | 1 |
| Remove cap from pre-flush syringe | 1 | |
| Attach kit assembly to injection site | | 1 |
| Attach pre-flush syringe to injection site | 1 | |
| Disconnect pre-flush syringe | 1 | |
| Remove cap from dose syringe | 1 | |
| Attach dose syringe to injection site | 1 | |
| Remove dose syringe | 1 | |
| Remove cap from post-flush syringe | 1 | |
| Attach post-flush syringe to injection site | 1 | |
| Disconnect kit assembly | | 1 |
| Disconnect post-flush syringe | 1 | |
| Total Makes and Breaks | 9 | 3 |

Thus, the number of makes and breaks required in this example is three while the number for a conventional method is nine, demonstrating a factor of three in required makes and breaks.

Accordingly, it is a primary object to provide methods and apparatus for preparing and using convenience kits for intravenous medical applications.

It is an object to provide methods and apparatus for preparing and using convenience kits for intravenous delivery of oncology drugs.

It is an object to provide methods and apparatus for preparing and using convenience kits for intravenous delivery of short half-life drugs.

It is an object to provide methods and apparatus for preparing and using convenience kits for intravenous delivery of emergency drugs.

It is an object to provide methods and apparatus for preparing and using convenience kits for intravenous delivery of drugs in home care situations.

It is an object to provide methods and apparatus for preparing and using convenience kits for clearing catheters in TPA type applications.

It is an object to provide methods and apparatus for preparing and using convenience kits for delivering antibiotics to a patient.

It is an important object to provide a sectioned package for kits according to the instant invention whereby one portion of the kit is partitioned from another portion such that one portion may be sterilized as a separate unit.

It is an object that the sectioned package be a tray having at least two recesses wherein objects are separately stored.

It is a more important object that the sectioned package comprises a plurality of bags, at least one being an inner sealed bag containing parts which are kept disparate from other parts in the associated outer bag.

It is a basic object that parts in the inner bag be sterilized while disposed therein.

It is a fundamental object that the outer bag be sealable, be able to be opened first by removing a tamper evident indicator and then resealed after each subsequent use.

It is a very important object to provide a kit system which provides access to two syringes.

It is also a very important object to provide a drug dispensing syringe as one of the two syringes.

It is yet another very important object to provide a prefilled flush or pre-fillable flush syringe as one of the two syringes.

It is an essential object to provide a method for selectively controlling pathways for fluid flow of the two syringes.

It is a compelling object to provide, for selectively controlling the pathways, a stopcock, affixed to each syringe, which provides a single pathway therefrom.

It is a more compelling object to provide a stopcock which assures fluid within each syringe is kept disparate from fluid within the other syringe.

It is a meaningful object to provide a clip for stabilizing the two syringes for single handed operation of the apparatus.

It is another meaningful object to provide a clip which may be used with syringes of various syringe barrel diameters.

It is a critical object to provide a kit which significantly reduces makes and breaks required for a predetermined procedure to lessen likelihood of contamination associated with such makes and breaks in a conventionally performed procedure.

It is a crucial object that connectable parts disposed in the inner bag be adjoined to reduce makes and breaks after sterilization.

It is another critical object that such adjoined parts be unreleasably affixed (unitized) to preclude separation in transport and storage.

It is a major object that the outer and inner bags be facilely openable for access filling the drug syringe and assembling parts disposed in the inner bag and parts disposed in the outer bag for sending an assembled system to a site of use.

It is a another major object that parts be accessible such that the drug syringe can be filled (e.g. in Pharmacy under a linear flow hood) under conditions which preclude contamination.

It is a yet another major object that the assembled system be replaced into the outer bag which is then resealed to be so transported to a site of use.

It is an object to provide a sterile cap for closing and protecting the output pathway of the system during transport to a site of use.

It is an object to provide method and apparatus for protectively storing a spent kit apparatus.

These and other objects and features of the present invention will be apparent from the detailed description taken with reference to accompanying drawings.

BRIEF DESCRIPTION OF THE DRAWINGS

FIG. 2A is a schematic drawing of a prior art three-way stopcock having three connecting ports and a rotatable core having a handle which is disposed to show a port closed thereat.

FIG. 2B is a schematic drawing of the three-way stopcock seen in FIG. 2A with the core and handle rotated to close a second port.

FIG. 2C is a schematic drawing of the three-way stopcock seen in FIGS. 2A and 2B with the core and handle rotated to close a third port.

FIG. 3A is a schematic drawing of a two-way stopcock found commonly in commerce and which is similar in structure and position to the three-way stopcock seen in FIG. 2A, but having stops which restrict core rotation (and port closures) to two positions, the first port closure position being seen in FIG. 3A.

FIG. 3B is a schematic drawing of the two-way stopcock seen in FIG. 3A with the core and handle rotated to close a second port.

FIG. 4A is a schematic drawing of a two-way stopcock having a core and handle and associated stops configured according to the present invention and closing the port indicated on the handle.

FIG. 4B is a schematic drawing of the two-way stopcock seen in FIG. 4A, but with the core and handle rotated to close another port.

FIG. 6A is a schematic drawing of a dual syringe and stopcock assembly with the stopcock core rotated to permit dispensing from a first syringe.

FIG. 6B is a schematic drawing of the dual syringe and stopcock assembly seen in FIG. 6A with the stopcock core rotated to permit dispensing for a second syringe.

FIG. 8 is a front elevation of another syringe holder or clip having a pair of syringe holding cavities, each cavity having a pattern which could hold one of three different barrels of three different syringe sizes.

FIG. 17A is a schematic representation of a separate kit which is provided for use in cases where a drug syringe is filled from a multi-dose source.

FIG. 19 is a perspective of the dual syringe/stopcock assembly seen in FIGS. 16-18, but with the stopcock oriented for dispensing fluid from the other syringe.

FIG. 25 is a schematic layout of part for a home-care drug delivery convenience kit according to the present invention.

DETAILED DESCRIPTION OF THE ILLUSTRATED EMBODIMENTS

In this description, the term proximal is used to indicate the segment of the device normally closest to the object of the sentence describing its position. The term distal refers a segment oppositely disposed. Reference is now made to the embodiments illustrated in FIGS. 1-25 wherein like numerals are used to designate like parts throughout. For parts which are similar but not the same as parts originally specified with a given number, a prime of the original numbers is used.

Figure 1:
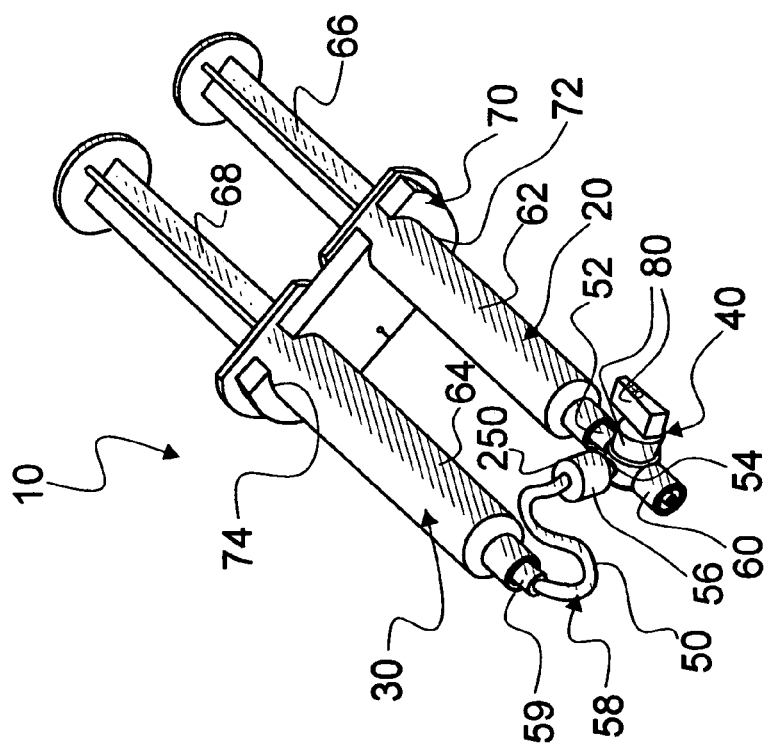
FIG. 1 is a perspective of a dual syringe assembly, comprising two syringes, a stopcock and a syringe clip, configured according to the instant invention.

While kits made according to the invention may be configured to provide assemblies for many medical procedures, such as those, for example, involved with injections of Adenosine, antibiotics and drugs for home-care, emergency and pediatrics, disclosure of an exemplary application in the area of hazardous drugs is herein selected to provide details of the instant invention while clearly demonstrating critically important safety and time and work saving features. Reference is now made to FIG. 1 wherein a convenience kit assembly 10 is seen to be readied for dispensing of fluids from a pair of syringes, numbered 20 and 30. Relative to a user, syringes 20 and 30 are interconnected through a stopcock 40 and micro-tubing set 50. Each syringe 20 and 30 may be a conventional commercially available medical syringe. One syringe, in particular syringe 30, may be a commercially available pre-filled flush syringe.

Stopcock 40 has three ports, a first port 52 being a female, preferably luer lock, connector which is securely affixed to syringe 20; a second port 54 also being a female, preferably luer lock, connector for connecting to a male connecting port 56 of tubing set 50. At an opposite end, tubing set 50 has a female, preferably luer lock, fitting 59 for secure attachment to syringe 30. Note that port 54 of stopcock 40 is disposed at right angles relative to port 52. Compliance and flexibility of tubing 58 of tubing set 50 permits syringe 30 to be aligned with syringe 20 for purposes disclosed in detail hereafter. A male, preferably luer lock, fitting 60 is exposed for attachment to a port, e.g. a catheter port, wherethrough fluid is dispensed to a patient.

Further each syringe 20 and 30 has a barrel 62 and 64, respectively, and a plunger rod 66 and 68, also respectively. Note that plunger rods 66 and 68 are disposed well outside barrels 62 and 64 indicating both syringes 20 and 30 are filled to a predetermined level (of liquid).

Alignment of syringe 20 to syringe 30 is maintained and assured by a clip 70 having a pair of substantially circular open slots 72 and 74, Slots 72 and 74 are shaped and formed to provide a releasable support for barrels 62 and 64, respectively. So configured, clip 70 provides a handle or grip whereby first and third fingers of a hand may be disposed outside a perimeter of barrels 62 and 64 with a middle finger of the same hand disposed between the barrels, thereby permitting a thumb of that hand to act upon either plunger rod as desired.

Fluid flow from assembly 10 is controlled by position of rotation of a core and handle 80 of stopcock 40. As seen in FIG. 1, output of syringe 20 is obstructed by the position of core and handle 80. As is explained in detail hereafter, rotation of core and handle 80 to a position obstructing outflow from syringe 30 opens outflow from syringe 20 to controllable permit selective dispensing of fluids from syringes 20 and 30 while keeping fluids within syringes 20 and 30 disparate.

Stopcocks

Generally, disposable stopcocks are well known and widely used in medical procedures. A three way stopcock 40' which is commercially available is seen in FIGS. 2A, 2B and 2C. Stopcock 40' has three ports 52, 54 and 60 which are substantially the same as stopcock 40 (see FIG. 1). As seen in FIG. 2A, within rotatable core 82 of core and handle 80, stopcock 40' comprises a "T" shaped pathway 84 disposed to obstruct fluid flow through port 54 and permit fluid transmission between ports 52 and 60. Note that pathway 84 can be considered to be comprised of two intersecting pathway segments, individually numbered 86 and 88. Pathway segment 86 is a through hole through core 82, while pathway segment 88 simply intersects pathway segment 86.

Rotating core and handle 80 to a stop associated with port 60, closes port 60 and permits fluid flow between ports 52 and 54 as seen in FIG. 2B. Rotating core and handle 80 to a stop associated with port 52 closes port 52 and permits fluid flow between ports 54 and 60, as seen in FIG. 2C. All of the above steps for stopcock 40' defines operation of stopcock 40' to be a three-way stopcock.

A stopcock 40" seen in FIGS. 3A and 3B is also commonly found in contemporary commerce. Generally ports 52, 54 and 60 of stopcock 40" are substantially the same as ports 52, 54 and 60 of stopcocks 40 and 40'. Note that rotation of core and handle 80 to a stop associated with port 54 as seen in FIG. 3A, closes port 54 and permits fluid flow between ports 52 and 60. However, rotation of core and handle 80 to a stop associated with port 60, closes port 60 and permits fluid flow between ports 52 and 54. In this manner, if port 60 is an output connecting port and ports 52 and 54 are connected to syringes, the syringe connected to port 54 cannot communicated directly with port 60. For this reason, a syringe connected to port 60 is usually affixed thereto to provide dilution fluid to contents of a syringe affixed to port 54. Following such dilution, contents of the syringe affixed to port 52 is dispensed through port 60.

However, in an application where hazardous drugs are to be kept disparate from flushing fluids, it is important that there is no fluid communication between syringes containing such liquids. Therefore, as seen in FIGS. 4A and 4B, core and handle 80 rotation is stopped such that there is no simultaneous communication between ports 52 and 54 along pathway segments 86 and 88. Note, that when core and handle 80 is disposed at a stop associated with port 54, port 54 is closed. When core and handle 80 is disposed at a stop associated with port 52, port 52 is closed. Since stopcock 40 is a two way stopcock, no communication is permitted between ports 54 and 52. In this manner, fluid disposed within port 54 is kept disparate from fluid disposed within port 52. Search of stopcocks currently in commerce revealed no such stopcock currently being in commerce. For this reason, inventor's were required to have a stopcock specially made to provide stops as defined for stopcock 40 in FIGS. 4A and 4B.

Figures 5A, 5B:
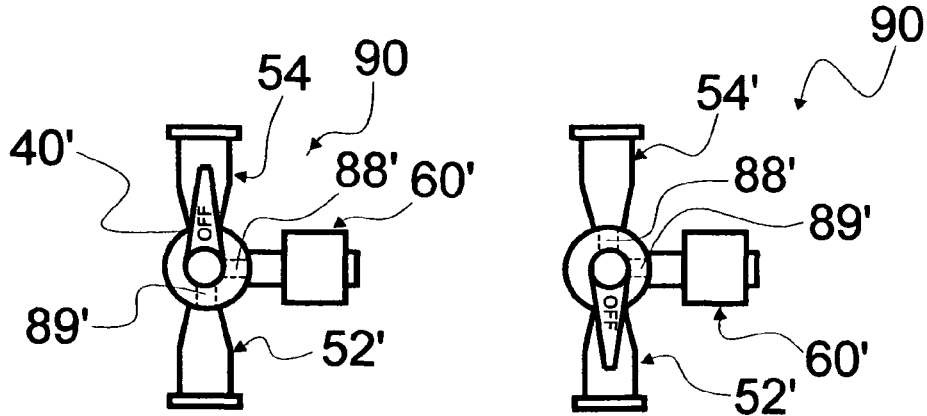
FIG. 5A is a schematic drawing of another two-way stopcock having a core and handle and associated stops configured according to the present invention and closing the port indicated on the handle.
FIG. 5B is a schematic drawing of the two-way stopcock seen in FIG. 5A, but with the core and handle rotated to close a different port.

Another stopcock 90 seen in FIGS. 5A and 5B, like stopcock 40, also keeps fluids associated with a pair of syringe ports 52' and 54' disparate. Note in FIG. 5A that port 54' is disposed in line with port 52'. However, a fluid pathway 86' made up of two connected orthogonally disposed segments 88' and 89' permits fluid flow from only one side port 52' or 54' to a common output port 60' at a time. Note in FIG. 5A that pathway 89' leads from port 52' to pathway 88' and output port 60' where core and handle 80 is at a stop associated with port 54'. Similarly, in FIG. 5B that pathway 88' leads from port 54' to pathway 89' and output port 60' when core and handle 40' is at a stop associated with port 52'. While port connections keep fluids of ports 52' and 54' disparate in the same manner fluids of ports 52 and 54 are kept disparate in stopcock 40 (see FIGS. 4A and 4B), dead space is decreased in stopcock 40" relative to dead space in stopcock 40 due to a pathway 89' which is half the length of pathway 86.

The need for a stopcock such as stopcock 40 (or 90) is exemplified by procedures for use as depicted in FIGS. 6A and 6B. In FIGS. 6A and 6B, arrows replace plunger rods showing direction of displacement of plunger rods. No arrow indicates no plunger rod movement. As a medical procedure associated with the instant invention involves, as a first step, delivering a dose from a syringe dedicated to providing a medication into a catheter port. As a second step, immediately dispensing a flush solution into the catheter port to flush both the catheter port and the catheter itself.

Such is accomplished by simply rotating core and handle 80 to occlude the output pathway of syringe 30, as seen in FIG. 6A, and displacing the plunger rod of syringe 20 in direction of arrow 92. Once desired contents of syringe 20 are dispensed, core and handle 80 of stopcock 40 are displaced to occlude output of syringe 20, as seen in FIG. 6B, and displacement of the plunger rod of syringe 30 provides flush solution to the catheter port and catheter.

Clips

Referring once more to FIG. 1, please note that syringe 20 and syringe 30 are aligned, one relative to the other, and held in alignment by clip 70. Clip 70 provides a releasable attachment for each syringe to improve facility of operation of two syringes held in a single hand. Note that a first and third finger may be placed about syringes 20 and 30 while a middle finger may be placed between the two syringes in such a manner that the thumb of the hand can be used to displace each syringe rod, 66 and 68. It is important that clip 70 holds each syringe securely, but releasably, such that either syringe may be removed from clip 70 for purposes which require a separated syringe, such as placing a syringe in a syringe pump.

Clips for assembly 10 may be made in many forms within the scope of the instant invention. Basic criteria for such clips are that the clip must provide sufficient stability for assembly 10 that two syringes may be facilely employed in a single hand and the syringe attachment must be secure, but releasable. Another optional requirement is that the clip be usable for a predetermined range of syringe barrel sizes.

Figure 7A:
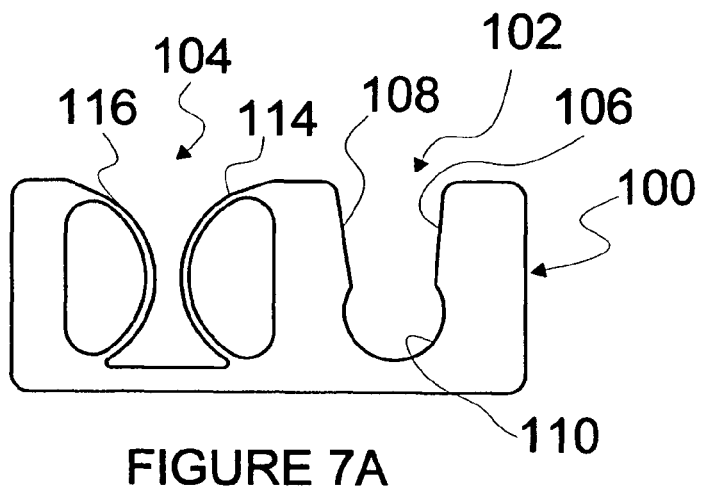
FIG. 7A is a front elevation of a dual syringe holder or clip.
Figure 7B:
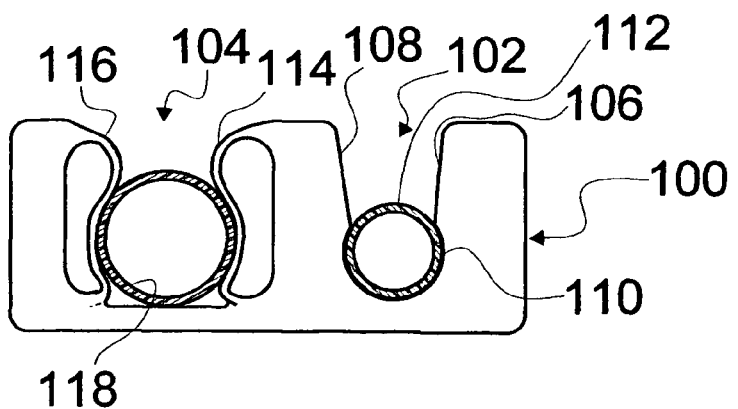
FIG. 7B is a front elevation of the dual syringe holder or clip seen in FIG. 7A with an outline of a syringe barrel inserted into a portion of the clip.

A syringe clip 100, made according to the instant invention, is seen in FIGS. 7A and 7B. Syringe clip 100 has a pair of slots 102 and 104 into which syringes may be displaced. As seen in FIG. 7A slot 102 comprises a pair of sides 106 and 108 which converge toward an open circular slot 110 which is sized and shaped to conform to a single predetermined syringe barrel size. Note, in FIG. 7B that a syringe barrel 112 (seen in cross section), is disposed in slot 102.

However, it is preferred that a clip be useful for more than one syringe barrel size. For this reason, slot 104 comprises a pair of compliant ribs 114 and 116 which forgivingly separate when a syringe barrel is displaced there into (see a cross section of a syringe barrel 118 disposed in slot 104. Ribs 114 and 116 must exert sufficient force against barrel 118 to retain barrel 118 in slot 104 once so disposed.

Clip 100 should be sufficiently thick to hold each inserted syringe barrel in position throughout a predetermined medical procedure associated with assembly 10. Clips like clip 100 may be injection molded using polypropylene.

A clip which is specifically designed to hold syringe barrels of a variety of sizes is seen in FIG. 8. As seen in FIG. 8, a clip 120 comprises two identical slots 122 and 124. As slots 122 and 124 are identical, only characteristics of slot 122 will be disclosed in detail. Slot 122 has a pair of converging sides 126 and 128 and a pattern which is sized and shaped to grasp a large syringe barrel (not shown) within edges 130, 132 and 134. Offset from slot 122 is a smaller circular slot 140 which is sized and shaped to grasp a smaller syringe barrel (also not shown). On an opposite side of slot 122 is yet another still smaller circular slot 150 sized and shaped to grasp a still smaller syringe (also not shown). In this manner, a single clip 120 may be used to hold one of three different sized syringe barrels within each slot 122 and 124. Similar to clip 100, clip 120 may be injection molded from polypropylene.

Figure 9:
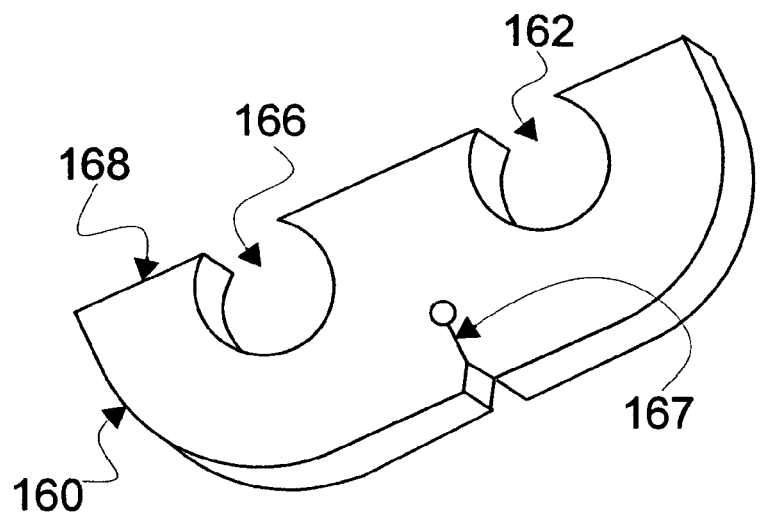
FIG. 9 is a perspective of a preferred dual syringe holder or clip.

A preferred clip 160 is seen in FIG. 9. Clip 160 comprises a pair of circular slots, numbered 162 and 166, which open superiorly to permit insertion (and retrieval) of a syringe barrel. The circular slots each have a diameter which is smaller than the smallest syringe barrel used in assembly 10. Further, clip 160 has a centrally disposed slit and hole 167 sized and shaped to permit clip 160 (and assembly 10) to be facilely suspended from tubing available at the site of use.

Clip 160 is preferably made of a substantially rigid closed cell foam material. As such clip 160 may be made by stamping out of a large sheet of material. While clip 160 may be made in various thickness (e.g. from 0.25 to 0.50 inches), a thickness of 0.375 inches is preferred to reduce likelihood of inadvertently concealing indicia generally placed on the barrel of a syringe. Closed cell foam, from which clip 160 is made, is particularly compatible for use as a barrel holder for assembly 10. The foam permits a tight grasp of an inserted barrel which is just larger than the diameter of the slot and yields when a much larger barrel is inserted to provide a stabilizing clasp upon the larger syringe barrel.

Figure 10:
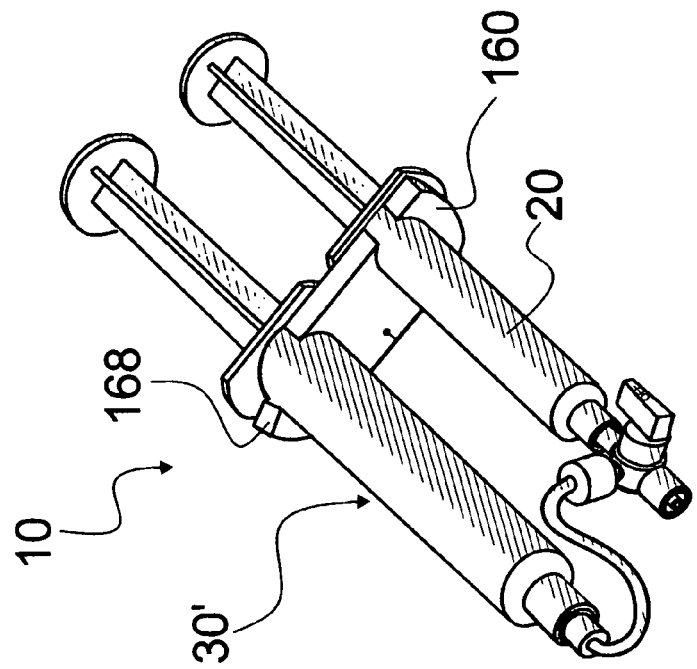
FIG. 10 is a perspective of a dual syringe assembly, comprising two syringes, a stopcock and a syringe clip, configured according to the instant invention, with an oversized syringe barrel disposed in one side of the clip.

An example of the manner in which clip 160 yields to a larger syringe is seen in FIG. 10 wherein an assembly 10 comprises a syringe 30' which is substantially larger in diameter than syringe 30 seen in FIG. 1. Note in FIG. 10 that an outside arm 168 is displaced from an original position as seen in FIG. 9. While insertion of larger syringe 30' causes displacement of arm 168, clip 160 still acts as an adequate stabilizing clasp about syringe 30'.

Kit Packaging

Figure 11A:
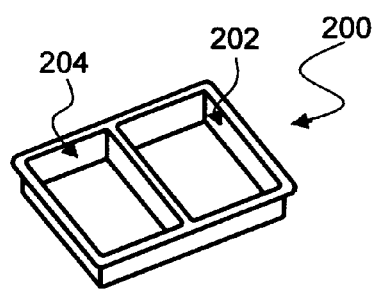
FIG. 11A is perspective of a divided tray for packaging parts of the instant invention separately.
Figure 11B:
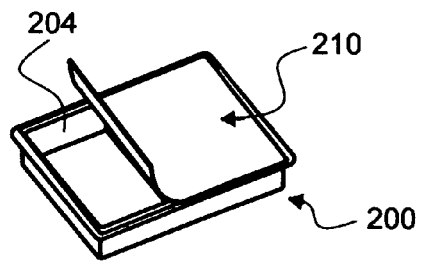
FIG. 11B is a perspective of the divided tray of FIG. 11A with a portion of the tray covered.
Figure 11C:
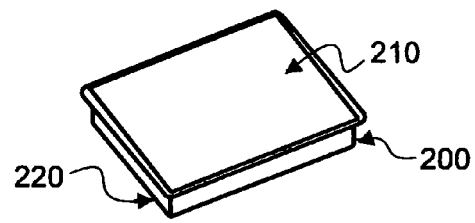
FIG. 11C is a perspective of the divided tray of FIG. 11A, entirely covered.

A kit according to the instant invention is assembled from an array of conventional products, most of which must be sterilized before use. To assure that as few post sterilization makes and breaks as possible occur, using items from a kit, each kit according to the instant invention is specially packaged. An example of such packaging is seen in FIGS. 11A, 11B and 11C. As seen in FIG. 11A, a receptacle (in this case tray 200) is seen to have two compartments, numbered 202 and 204. Each compartment has a size and shape to fully contain a group of components specified for a particular purpose of the kit.

In this case, compartment 202 is dedicated to holding components which are sterilized after being placed in the kit. In this manner, a cover 210 provides a seal above components to be sterilized after being disposed in compartment 202. Generally, components, to be sterilized, are displaced into compartment 202, sealed there within and sterilized by a predetermined method of sterilization (such as gamma radiation, ethylene oxide, etc.). After such sterilization, other components which do not require in tray sterilization are displaced into compartment 204 and cover 210 is completely sealed to tray 200 (as seen in FIG. 11C) to provide a deliverable container 220.

Figure 12:
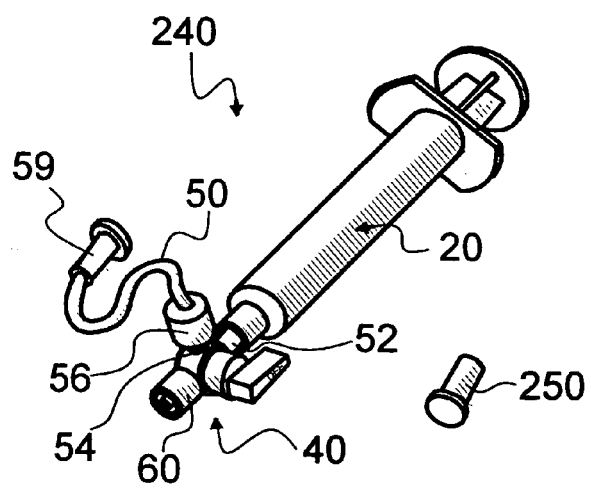
FIG. 12 is a perspective of a set of parts gathered and assembled to be sterilized.

One of the primary objects of the instant invention is to decrease numbers of makes and breaks after sterilization to as few as possible. For this purpose, as much as possible, parts which are joined for use in assembly 10 are securely affixed one to another prior to being sterilized. It is important that these parts remain affixed one to another through all phases of kit use. For this reason, it is recommended that these parts be unitized parts, becoming even as a single unitized part 240 (i.e. be adhesively interconnected where possible), as seen in FIG. 12. Where such is not possible the parts should be tightly mechanically secured. As an example, syringe 20 is securely affixed to port 52 of stopcock 40. Similarly, port 54 of stopcock 40 is affixed to a male fitting 56 of extension set 50. A female fitting 59 and a male fitting 60 are left open for purposes which are disclosed in detail hereafter. As a cap 250 may be later used as a sterility protecting cover after a syringe 20 filling procedure, cap 250 is included with the unitized parts.

Figure 13:
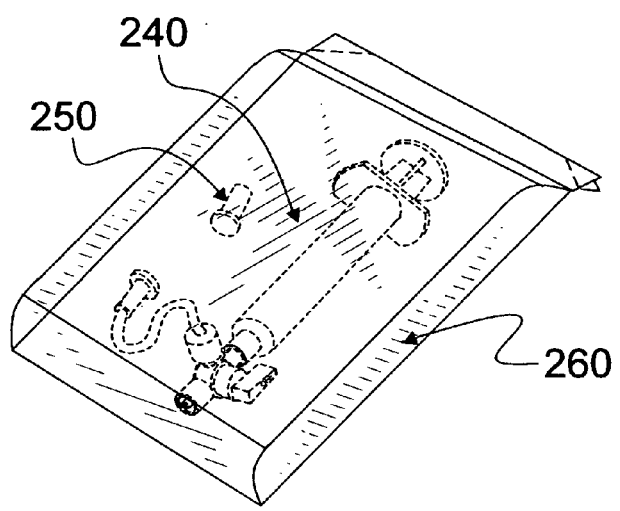
FIG. 13 is a perspective of the set of parts seen in FIG. 12 disposed in a sealed bag or wrap.
Figure 14:
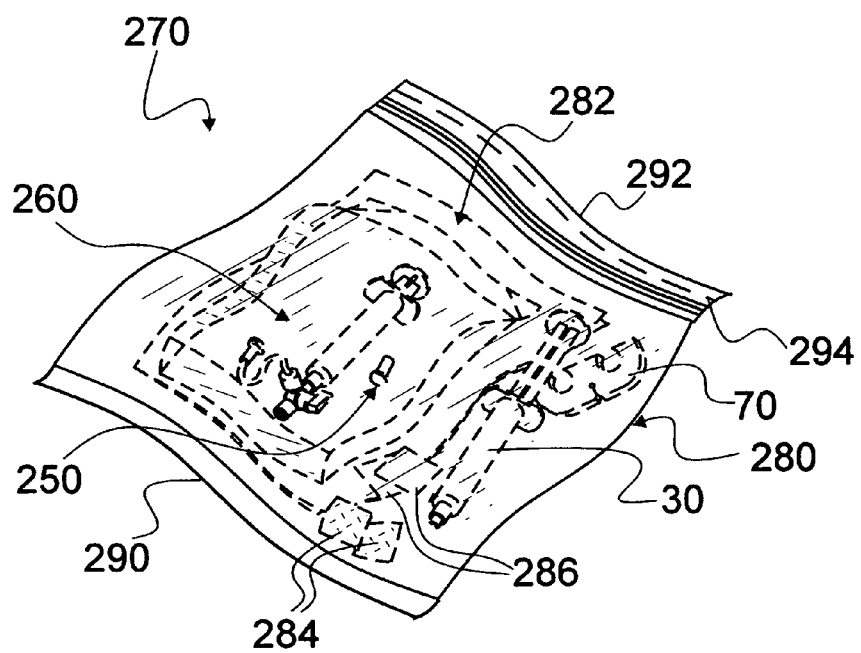
FIG. 14 is a perspective of the sealed bag of parts seen in FIG. 13 disposed in a resealable bag with other parts to form a kit.
Figure 15:
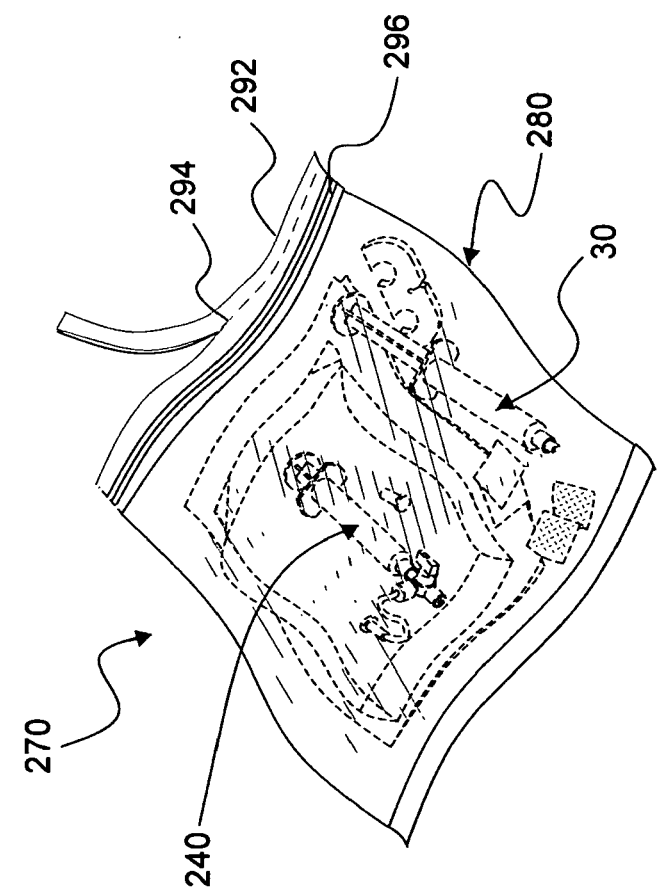
FIG. 15 is a perspective of the sealed bag of parts seen in FIG. 14, with a tamper evident strip partially torn away to provide access to the resealable bag.

A preferred mode of packaging is seen in FIGS. 13-15. Note that a unitized part 240 and a cap 250 are disposed and sealed within a sterilizable peel pouch or wrap 260 wherein contained parts are processed by gamma radiation, ethylene oxide or other sterilization process.

A fully packaged hazardous drug kit 270 is seen in FIG. 14. Note that peel pouch or wrap 260 is fully enclosed within a resealable bag 280. Within bag 280, other kit items are also stored, such as a flush syringe 30, a clip 70, a protective pad or crib sheet 282, a pair of gauze pads 284 and alcohol wipes 286, all of which are important items used within hazardous drug kit 270.

Crib sheet 282 is used as a protective cover over work areas associated with drug and flush dispensing, having a plastic backing for extra protection. While crib sheet 282 is a part of kit 270 for convenience, it is optional. Such may also be said of gauze pads 284 and alcohol wipes 286 as all of these items are also usually readily available at a drug dispensing site. However, time taken to gather and assemble such items may prove expensive and quite undesirable when dealing with conditions pertaining to dispensing hazardous drugs.

Note that flush syringe 30 is not included in items sterilized in peel pouch or wrap 260. Generally, a flush syringe 30 has already been prepared under sterile conditions or previously sterilized and may not be able to withstand rigors of sterilization. For such reasons, all items of kit 270 which need not be further sterilized are contained within bag 280 outside peel pouch 260.

Bag 280 fills a number of needs relative to hazardous drug dispensing. First, bag 280 comprises a seal at a filling end 290 and another seal at a dispensing end 292. End 292 comprises a tamper evident tear strip 294 which must be removed for access to items within bag 280. A partially removed tear strip 294 is seen in FIG. 15. Removal of tear strip 294 provides access to a section 296 having a pair of conforming sides which may be zipped together to provide a resealed bag 280 after each use. In this manner, protection can be provided for items during transit from sites of filling, such as pharmacy, to a site of use and further to a site of final disposal, such as into a biohazard waste container.

Methods of Preparation and Use

Figure 16:
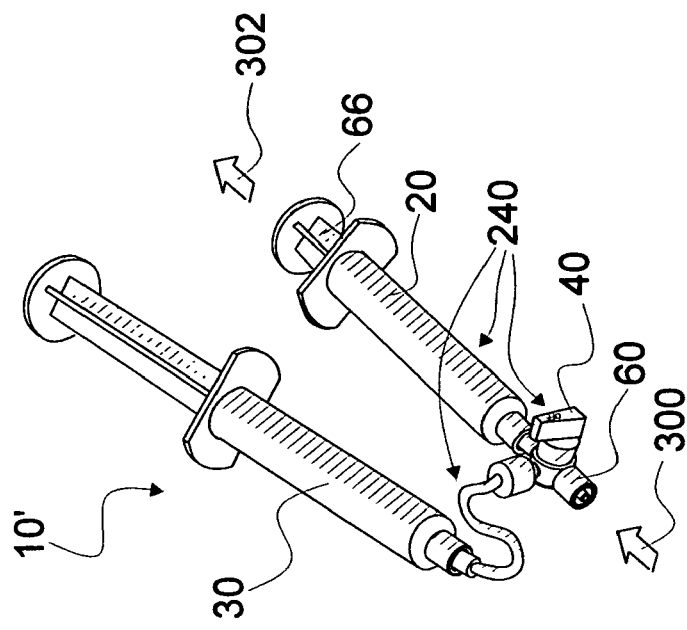
FIG. 16 is a perspective of a dual syringe/stopcock assembly configure according to the present invention with the stopcock disposed for filling a preselected syringe.

Reference is now made to FIG. 16 wherein an assembly 10', assembly 10 without clip 70, is seen. Note that assembly 10' is constructed by attaching a pre-filled flush syringe 30 to a unitized part 240. Of course, to construct assembly 10', items within bag 280, tear strip 294 must be removed from bag 280 to provide access through section 296. (See FIGS. 14 and 15). Peel pouch 260 and flush syringe 30 are then removed. Then syringe 30 may be securely affixed to unitized part 240, preferably via luer lock connection. To reduce likelihood of contamination, such an attachment should be performed in a clean, controlled environment, such as within a safe area of a laminar flow hood.

With stopcock 40 disposed for filling syringe 20, as seen in FIG. 16, male fitting 60 of stopcock 40 is affixed to a source of drug to be transferred to syringe 20 according to institutional protocol. Such protocol usually involves swabbing with alcohol pads, such as pads 286, see FIG. 15, the reason for which alcohol pads are made a part of kit 270.

Figure 17:
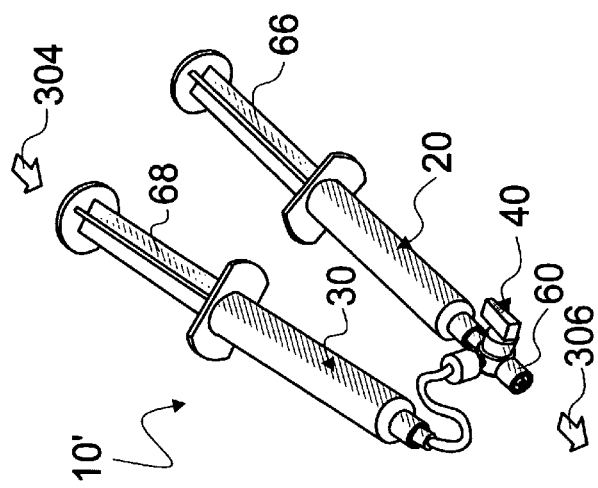
FIG. 17 is a perspective of the dual syringe/stopcock assembly seen in FIG. 16, but wherein the predetermined syringe has been filled and stopcock reoriented to permit dispensing of fluid from the other syringe.
Figure 24:
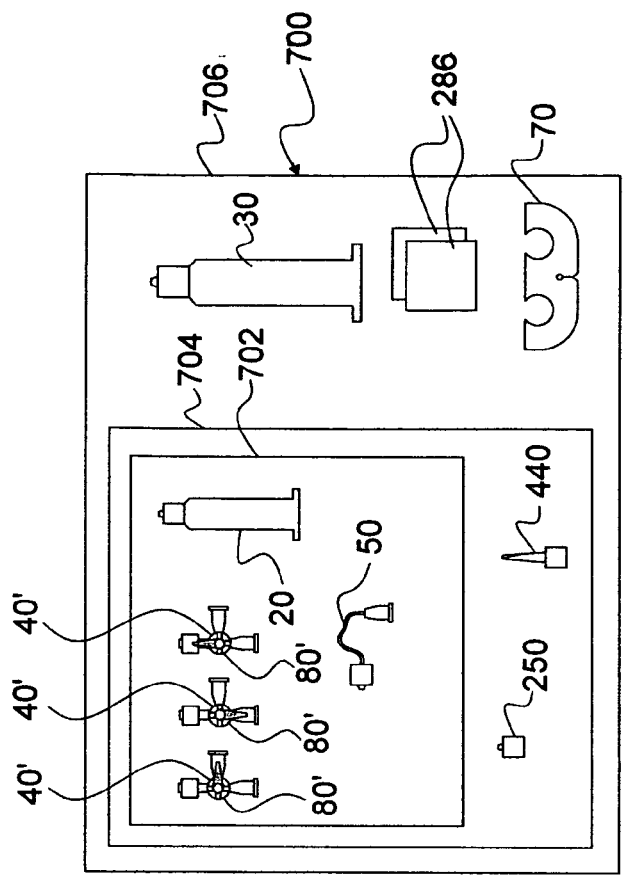
FIG. 24 is a schematic layout of parts for dilution convenience kit according to the present invention.

As is well understood by clinicians trained in use of syringes, medication or drug is drawn into syringe 20 in direction of arrow 300 by retracting plunger rod 66 in direction of arrow 302. Once syringe 20 is filled, and primed, a predetermined amount of flush solution is dispensed from pre-filled flush syringe 30 as seen in FIG. 17. To accomplish this, stopcock 40 is disposed to permit fluid flow from syringe 30 to fitting 60. Plunger rod 68 is displaced in direction of arrow 304 to dispense flush solution outward from fitting 60 in direction of arrow 306. It is recommended that, for 10 ml flush syringes, approximately one milliliter of flush solution be dispensed to flush fitting 60. Note that by flushing fitting 60 hazardous drug resident at fitting 60 is replaced with flush solution.

In some cases drug accessed to fill syringe 20 is provided from a multi-dose source. In such a case, it is undesirable to dispense flush into the multi-dose and thereby dilute or otherwise contaminate contents of the multi-dose source. For this reason, an intermediate assembly 400, seen in FIG. 17A, is provided to permit flushing fitting 60 without dispensing flush into the multi-dose source.

As seen in FIG. 17A, assembly 400 comprises a "T" shaped interconnection 410 having three interconnecting fittings, numbered 412, 414 and 416. Fitting 412 is preferably a female luer lock fitting for securely, but releasably connecting to fitting 60 (see FIG. 17) of assembly 10'. To fitting 414, a check valve 420 is affixed to only permit fluid flow in direction of arrow 422. Tubing extending distally from check valve 420 is shown, by example, to include an access tube 430 and vial access device 440. Of course other parts and devices may be used as prescribed institutional protocol for access to the multi-dose source.

Fitting 416 is securely connected to another check valve 450, which is further securely attached to a waste container 460. Waste container 460 should be of sufficient size to hold all fluid which is dispensed from that plurality of assembly 10' units required to fully empty the multi-dose source. Note that waste container 460 may have many forms including a plastic bag and a syringe.

Care should be taken to assure as little mixing of flush solution with medicant dose as possible for succeeding uses of assembly 10' units. For this reason, it is recommended to use a procedure similar to the following:

Before connecting fitting 60 to fitting 412, draw sufficient gas (air) into syringe 20 to fully expel fluid from "T" 410. Connect fitting 60 to fitting 412 and set stopcock 40 to permit flow from syringe 20 to fitting 60. Dispense the gas from syringe 20 into "T" 410 and therefrom to wasted container 460. Draw desired, measured dose into syringe 20. Set stopcock 40 to permit flow from syringe 30 to fitting 60. Dispense a predetermined volume of flush solution from syringe 30 through fitting 60, into "T" 410 and waste container 460.

Once syringe 20 is filled and fitting 60 is flushed, stopcock 40 should remain in the open flush pathway state. Fitting 60 should be capped (preferably with provided cap 250 (see FIG. 12). Then all unused parts and assembly 10', with a cap in place, should be returned to resealable bag 280. Bag 280 is resealed for safety in transport to site of use.

Figure 18:
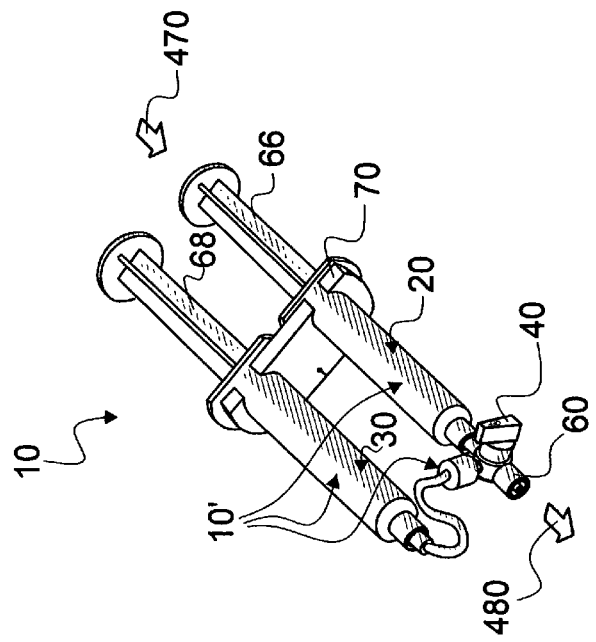
FIG. 18 is a perspective of the dual syringe/stopcock assembly seen in FIGS. 16 and 17, but with the stopcock disposed for dispensing fluid from the predetermined syringe.

At the site of use, assembly 10' is removed from bag 280 and clip 70 is affixed thereto (as seen in FIGS. 1 and 18) to form assembly 10. Note that clip 70 stabilizes syringes 20 and 30 relative to one another, permitting single handed operation when dispensing either of the two syringes, 20 and 30. Alcohol wipes 286, gauze pads 284 and crib sheet 282 are put in place and used per institutional protocol. Fitting 60 is securely, but releasably affixed to a receiving catheter or other receptacle fitting. Stopcock 40 is set to provide an open pathway from syringe 20 to fitting 60. Plunger rod 66 is displaced in direction of arrow 470 to dispense medicant through fitting 60 in direction of arrow 480 for its designated purpose, as seen in FIG. 18. Note that by grasping assembly 10 about syringes 20 and 30 with the index and third fingers and placing the middle finger of a hand between syringes 20 and 30, the thumb of the hand can facilely displace plunger rods 66 and 68.

Figure 21:
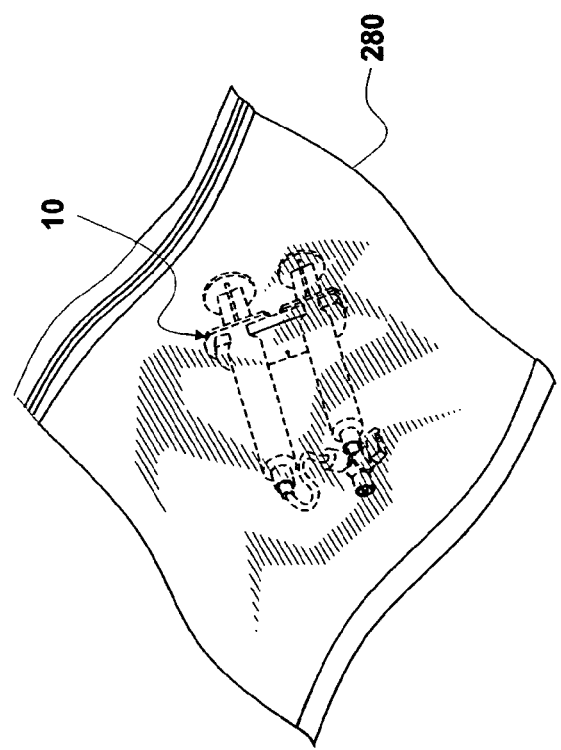
FIG. 21 is a perspective of the dual syringe/stopcock assembly wherein both contents of both syringes have been dispensed and returned to the resealable bag.
Figure 22:
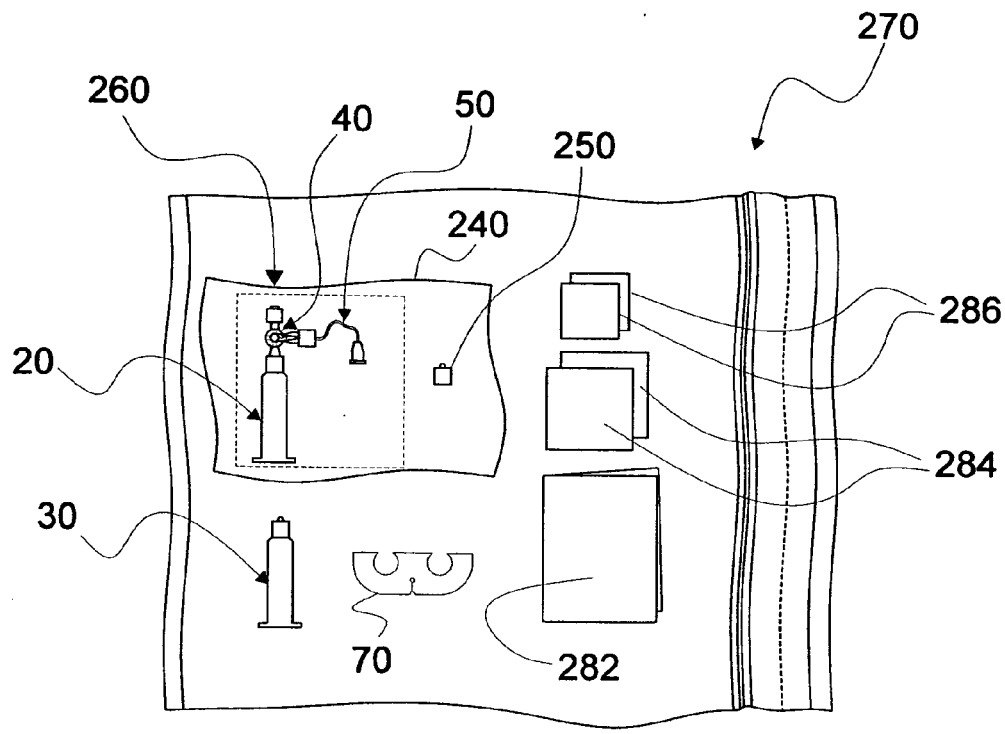
FIG. 22 is a schematic layout of parts for a hazardous drug convenience kit according to the present invention.

Once a desired amount of fluid of syringe 20 is displaced therefrom, stopcock 40 is displaced to obstruct flow of fluid from syringe 20 and open the fluid flow pathway from syringe 30. Generally, sufficient fluid is dispensed from syringe 30 by displacing plunger rod 66 in direction of arrow 490 to flush fitting 60 and a catheter or other communicating fluid line, as seen in FIG. 19. For a single use application of assembly 10, plunger rods 66 and 68 are fully displaced, spent assembly 10 is returned to resealable bag 280. Bag 280 is resealed (as seen in FIG. 21) and bag 280 its contents are delivered to an appropriate waste container per institutional protocol.

Figure 20:
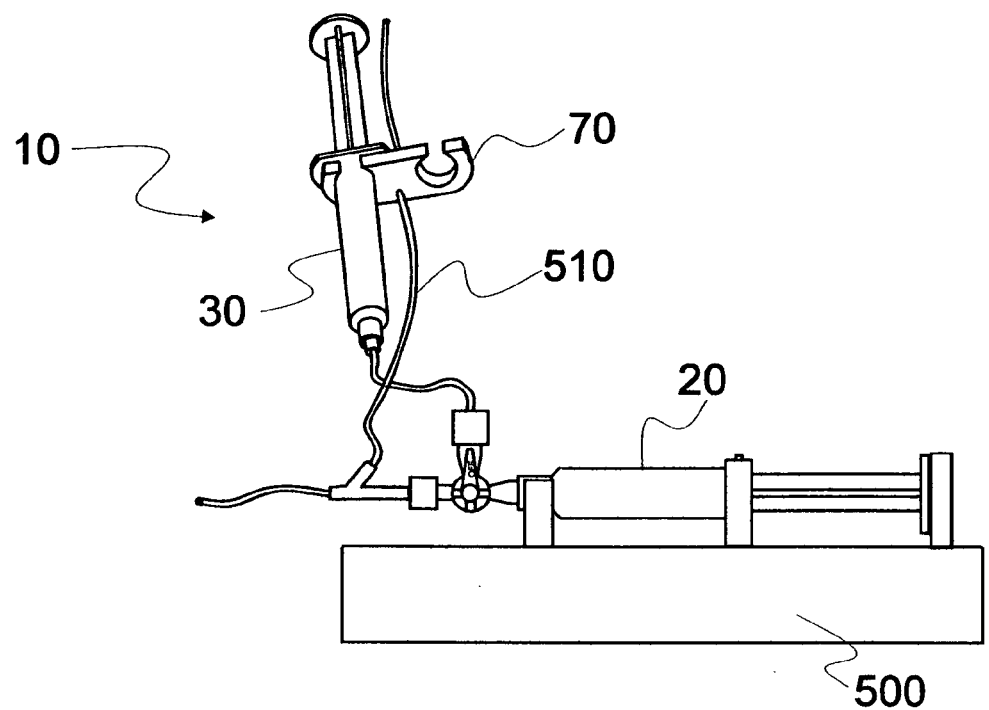
FIG. 20 is a schematic representation of a predetermined syringe being displaced from a clip of a dual syringe/stopcock assembly and disposed in a syringe pump, while the rest of the assembly has been releasably affixed to a tube via a slotted hole in the clip for convenience.

Medication and flush delivery may not always be performed manually. For example, in some cases, it may be desirable to use a syringe pump to provide a slow, controlled infusion. In such a case, the facility of clip 70 is demonstrated. For example, as seen in FIG. 20, a syringe 20 has been removed and displaced into a syringe pump 500. The remaining portion of assembly 10 is affixed to a hanging tube 510 by slit and hole 167 (see FIG. 9) for convenience.

Areas of Application

While the above disclosure has been dedicated to a kit associated with delivery of hazardous drugs, the instant invention has far broader application. As seen in FIGS. 22-25, there is opportunity for use of such kits in a wide range of applications that include dose dispensing followed by a flush. Kit 270 is duplicated schematically in FIG. 22 for reference. Note in kit 270 that a presterilized portion of kit 270 is provided in a sealed pouch or wrap 260. Contained in pouch 260 are a syringe 20, an extension set tubing set 50, stopcock 40 and a cap 250. Syringe 20, tubing set 50 and stopcock 40 are joined and unitized for convenience and as a precaution against contamination from post sterilization assembly.

Other parts assembled for kit 270 include a pre-filled flush syringe 30, a pair of alcohol wipes 286, two gauze pads 284 and a crib pad 282. Again to lower likelihood of contamination when connecting flush syringe 30 with tubing set 50, such is recommended to be done under controlled conditions, such as under a laminar flow hood in pharmacy at the same time syringe 20 is filled with a medicant Other parts, for which no instructions are provided, are available as a convenience, to be used per institutional protocol. All of the parts are enclosed and sealed in a tamper evident, resealable bag 280 for use as disclosed supra.

A very important application of the instant invention relates to delivery of Adenosine. As is well known in cardiovascular art, Adenosine is a drug which, properly administered, is effective in treating a dangerous form of dysrythmia. It is also well known that Adenosine is a drug having a short half-life after injection. For this reason, it is critical that a dose of Adenosine be followed quickly with a rapid flush to assure transporting the drug to a predetermined target area (e.g. atria of the heart). In some institutions, it is common practice to have a pair of nurses operating in tandem to first deliver Adenosine by a first nurse followed by a rapid flush delivered by a second nurse. Use of a kit afforded by the instant invention permits a single nurse to delivery both drug and flush in a timely manner. Simply stated, Adenosine in syringe 20 (see FIG. 18) is delivered. Then, by switching stopcock 40 with a free hand to open the pathway from syringe 30 (see FIG. 19), flush is delivered efficaciously immediately thereafter, using but a single hand for fluid delivery.

Figure 23:
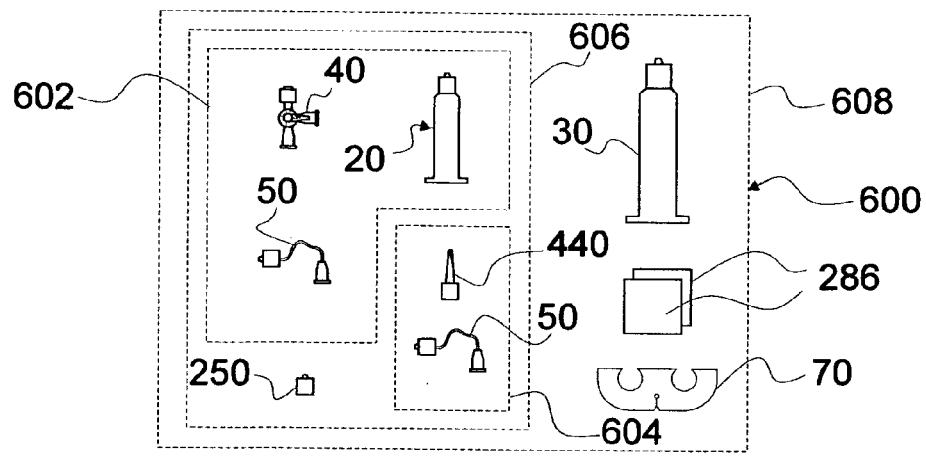
FIG. 23 is a schematic layout of parts for an Adenosine convenience kit according to the present invention.

Parts provided in a kit 600 for adenosine are seen schematically in FIG. 23. Parts which are joined and unitized prior to sterilization, 50 as disclosed supra, are seen surrounded by a dashed line 602 and include a stopcock 40, a syringe 30 and a tubing set. In addition, a vial access device 440 and another tubing set 50, seen surrounded by dashed line 604, may be provided and also joined together and unitized. As previously disclosed, a cap 250 may also be included. Thus, the set of parts enclosed by dashed line 606 are placed in a sealed pouch, such as pouch 260 (see FIG. 14) and sterilized. Other parts associated with kit 600 include a pre-filled flush syringe 30 and a pair of alcohol wipes 286 which are displaced into a resealable bag 280 to complete kit 600.

Use of stopcock 40 does not permit contents of pre-filled syringe 30 to be used as a diluent for contents of syringe 20. For this reason a three way stopcock 40' is provided in a kit 700 seen in FIG. 24. Two stopcock images are seen in dashed lines to show various positions of stopcock core and handle 80' whereat one of the three stopcock ports is closed at each position. A stopcock, such as stopcock 40', is widely available commercially. Those parts enclosed by dashed line 702 syringe 20, stopcock 40' and tubing set 50 are joined as disclosed supra and unitized. Parts enclosed by dashed line 704, including in addition cap 250 and vial access device 440 are displaced into a sealed pouch or wrap 260 (see FIG. 14) and sterilized. Other parts of kit 700 include a pre-filled flush syringe 30, alcohol wipes, generally numbered 286, and a clip 70 are displaced into a resealable bag 280 and sealed to provide kit 700.

A stopcock 40 may be used to replace stopcock 40' of kit 700 to form kit 800 for use in home care applications. Note that dashed line 802 encloses parts joined and unitized in kit 800. Dashed line encloses parts sterilized and placed in a pouch 260 (see FIG. 14). The other parts, enclosed by dashed line 806 are displaced into a resealable bag 280 and sealed to provide kit 800.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for preparing and using a kit for measuring, filling and dispensing medication and flush solutions to patients through connections to patient lines and catheters while improving safety and efficacy of such procedures by requiring fewer post sterilization makes and breaks than like procedures performed with conventional components and methods, by facilitating dispensing of flush solutions, by providing for flushing of patient line and catheter connecting fittings before breaking such connections, by providing resealable, tamper evident kit packaging which permits sealed transport of kit parts after initial opening and parts use, by providing a two syringe assembly which is operable by a single hand and by providing for selectively dispensing from each of the two syringes while obstructing flow from the other syringe, said method employing the following steps:

providing a resealable, tamper evident bag for containing and transporting items used to perform a predetermined medical procedure;

providing items of the kit comprising:

at least one sealed pouch wherein each part disposed therein is sterilized before being displaced into said bag, at least one sealed pouch containing a plurality of individual parts interconnected and unitized to preclude further post-sterilization assembly;

said plurality of parts comprising a medical dose syringe, a stopcock affixed to the syringe to selectively obstruct and permit fluid flow from the dose syringe and to an extension set by which a pre-filled flush syringe is to be affixed and aligned for use with the medical dose syringe, said stopcock having a free fitting whereby the unitized parts are connected to a medical connector; and a pre-filled flush syringe;

after assuring positive visual inspection of the resealable, tamper evident bag, removing a tamper evident section of the bag to permit access inside thereof;

in a controlled, clean environment, opening the resealable bag to access the at least one sealed pouch containing unitized parts;

retrieving the pre-filled flush syringe from the resealable bag and affixing the pre-filled flush syringe to said extension set to construct a two syringe assembly whereby the pre-filled flush syringe may be aligned with the medical dose syringe;

affixing the free fitting to a source of medication;

setting the stopcock to provide a pathway from said free fitting to said medical dose syringe;

filling the medical dose syringe with a predetermined volume of medication;

setting the stopcock to provide a pathway from the pre-filled flush syringe to the free fitting;

dispensing a predetermined volume of flush through the free fitting;

detaching the free fitting from the source of medication;

capping the free fitting to ready the two syringe assembly for transport; and returning unused parts of the kit and the two syringe assembly to the resealable bag and resealing the bag preparatory for transporting the bag to a site of use.

2. The method for preparing and using a kit for measuring, filling and dispensing medication and flush solutions to patients through connections to patient lines and catheters according to claim 1, comprising the additional steps of:

at the site of use, opening the bag by breaking the seal of the resealable bag;

retrieving the two syringe assembly from the bag;

displacing from the bag, other parts of the kit including a clip used for dispensing medication;

affixing the clip to barrels of the two syringes to stabilize the two syringe assembly;

removing a cap from the two syringe assembly;

following institutional protocol, affixing the free fitting of the two syringe assembly to a predetermined connector wherethrough medication is delivered;

setting the stopcock to permit fluid flow from the medical dose syringe to the free fitting;

dispensing a desired volume of medication from the medical dose syringe;

setting the stopcock to obstruct flow from the medical dose syringe and permit flow from the pre-filled flush syringe to the free fitting; and dispensing a predetermined volume of flush to the medical connector through the free fitting.

3. The method for preparing and using a kit for measuring, filling and dispensing medication and flush solutions to patients through connections to patient lines and catheters according to claim 2, comprising the following additional steps:

disengaging the free fitting from the medical connector;

capping the free fitting;

returning the two syringe assembly to the resealable bag;

returning other used kit items to the resealable bag;

resealing the resealable bag; and disposing the sealed resealable bag following institutional protocol.

4. The method for preparing and using a kit for measuring, filling and dispensing medication and flush solutions to patients through connections to patient lines and catheters according to claim 1 wherein the dispensing step further comprises holding the two syringe assembly in a single hand and actuating plunder rods of each syringe with a thumb of that hand.

5. The method for preparing and using a kit for measuring, filling and dispensing medication and flush solutions to patients through connections to patient lines and catheters according to claim 1 comprising an additional step of dispensing a predetermined volume of flush solution through the free fitting before the step of setting the stopcock to permit fluid flow from the medication dose syringe to the free fitting.

* * * * *